(12) United States Patent
Doi et al.

(10) Patent No.: US 9,693,982 B2
(45) Date of Patent: Jul. 4, 2017

(54) COMPOSITION FOR AMELIORATION OF HYPOALBUMINEMIA

(71) Applicant: OTSUKA PHARMACEUTICAL FACTORY, INC., Tokushima (JP)

(72) Inventors: Masako Doi, Tokushima (JP); Masuhiro Nishimura, Tokushima (JP); Nozomi Tamura, Tokushima (JP)

(73) Assignee: OTSUKA PHARMACEUTICAL FACTORY, INC., Tokushima (JP)

(*) Notice: Subject to any disclaimer, the term of this patent is extended or adjusted under 35 U.S.C. 154(b) by 38 days.

(21) Appl. No.: 14/287,954

(22) Filed: May 27, 2014

(65) Prior Publication Data

US 2014/0309306 A1 Oct. 16, 2014

Related U.S. Application Data

(62) Division of application No. 13/638,358, filed as application No. PCT/JP2011/058365 on Mar. 31, 2011, now abandoned.

(30) Foreign Application Priority Data

Apr. 7, 2010 (JP) .................. 2010-089077

(51) Int. Cl.
  *A61K 31/198* (2006.01)
  *A23L 2/52* (2006.01)
  *A23L 33/175* (2016.01)

(52) U.S. Cl.
  CPC .............. *A61K 31/198* (2013.01); *A23L 2/52* (2013.01); *A23L 33/175* (2016.08)

(58) Field of Classification Search
  None
  See application file for complete search history.

(56) References Cited

U.S. PATENT DOCUMENTS

| 3,960,942 A | 6/1976 | Hirsbrunner et al. |
| 6,203,820 B1 | 3/2001 | Vickery |

(Continued)

FOREIGN PATENT DOCUMENTS

| DE | 2013026 A1 | 10/1971 |
| EP | 0700681 A1 | 3/1996 |

(Continued)

OTHER PUBLICATIONS

Nishitani, Pharmacological activities of branched-chain amino acids: specificity of tissue and signal transduction, Biochemical and Biophysical Research Communications, 2004, 313, pp. 387-389.*

(Continued)

*Primary Examiner* — San-Ming Hui
*Assistant Examiner* — Andrew Lee
(74) *Attorney, Agent, or Firm* — Greenblum & Bernstein, P.L.C.

(57) ABSTRACT

The present invention is directed to a composition for ameliorating hypoalbuminemia containing a branched-chain amino acid(s) as an active ingredient(s), wherein the composition contains leucine and/or isoleucine as the active ingredient(s) and does not contain valine. As the above branched-chain amino acid(s), leucine and isoleucine are preferably contained. The mass ratio of leucine to isoleucine described above is preferably from 0.1 to 10. As the above branched-chain amino acid(s), either leucine or isoleucine alone may be contained. The present invention is suitably used as an infusion formulation, an oral formulation or a food or drink.

7 Claims, 1 Drawing Sheet

(56) References Cited

U.S. PATENT DOCUMENTS

| | | | |
|---|---|---|---|
| 6,713,501 | B1 | 3/2004 | Walser |
| 7,674,485 | B2 | 3/2010 | Bhaskaran et al. |
| 2002/0131996 | A1 | 9/2002 | Zasloff et al. |
| 2005/0008711 | A1 | 1/2005 | Di Pierro |
| 2007/0026108 | A1 | 2/2007 | Foulger |
| 2008/0161399 | A1* | 7/2008 | Moriwaki et al. ............ 514/561 |

FOREIGN PATENT DOCUMENTS

| | | |
|---|---|---|
| EP | 1358877 A1 | 11/2003 |
| JP | 62-135420 | 6/1987 |
| JP | 3712539/11-171763 | 8/2005 |
| JP | 2008-88113 | 4/2008 |

OTHER PUBLICATIONS

Ijichi, Branched-chain amino acids promote albumin synthesis in rat primary hepatocytes through the mTOR signal transduction system, Biochemical and Biophysical Research Communications, 2003, 303, pp. 59-64.*

Russian Office Action issued with respect to application No. 2012146985/15, mail date is Jan. 26, 2015.

Olde Damink et al. Isoleucine Infusion During "Simulated" Upper Gastrointestinal Bleeding Improve Liver and Muscle Protein Synthesis in Cirrhotic Patients, Hepatology, vol. 45, No. 3, 2007.

Examination Report issued with respect to New Zealand Application 602642, mail date is Jan. 6, 2014.

International Preliminary Report on Patentability and Written Opinion of the Searching Authority from PCT/JP2011/058365 dated Nov. 15, 2012.

Nishimura et al., "Tissue Distribution of mRNA Expression of Human Cytochrome P450 Isoforms Assessed by High-Sensitivity Real-Time Reverse Transcription PCR", Yakugake Zasshi, vol. 123, 2003, pp. 369-375.

M. Nishimura et al., "Evaluation of mRNA expression of Human drug-metabolizing enzymes and transpoters in chimeric mouse with humanized liver", Xenobiotica, 2005, pp. 877-890, vol. 35.

M. Nishimura et al., "Tissue-specific mRNA expression profiles of human nuclear receptor subfamilies", Drug Metab. Pharmacokinet., 2004, pp. 135-149.

M. Nishimura et al., "Evaluation of gene induction of drug-metabolizing enzymes and transporters in primary culture of human hepatocytes using high-sensitivity real-time reverse transcription PCR", Yakugaku Zasshi, 2002, pp. 339-361, vol. 122.

Chiori Ijiichi et al., "Branched-chain amino acids promote albumin synthesis in rat primary hepatocytes through the mTOR signal transduction system", Biochem. Biophys, Res. Commun., 2003, pp. 59-64, vol. 303.

Tomoaki Tomiya et al., "Treatment with leucine stimulates the production of hepatocyte growth in vivo", Biochem. Biophys, Res. Commun., 2004, pp. 772-777, vol. 322.

"Prooceedings of Okayama Prefectural Junior College", Okayama Prefectural Junior College Kiyo, 1990, pp. 51-54, vol. 33, No. 2.

Misako Okita et al., "Effects of Valine on 15N Incorporation into Serum and Tissue Protein and Non-protein Fractions Following 15N-L-Leucine Administration to Normal and Liver-Injured Rats", J. Nutr. Sci. Vitaminol, 1989, pp. 559-567 (566), vol. 35.

Kazutomo Imabori et al., "Seikagaku Jiten 3rd edition, 5th print, Tokyo Kagaku Dojin", 2002, pp. 67-68.

Search report from International Application No. PCT/JP2011/058365, mail date is May 17, 2011.

European Search Report issued with respect to application No. 11765816.1, mail date is Dec. 4, 2015.

Shinobu Nishitani et al., "Pharmacological activities of branched-chain amino acids: augmentation of albumin synthesis in liver and improvement of glucose metabolism in skeletal muscle", Hepatology Research 30S, 2004, S19-S24.

Shinobu Nishitani et al., "Branched-chain amino acids improve glucose metabolism in rats with liver cirrhosis", The American Physiological Society, vol. 288, No. 6, Jun. 2005, pp. G1292-G1300.

Taiwanese Office Action issued with respect to application No. 100112031, mail date is Oct. 7, 2014.

Komatsu et al., "Effects of Caloric Intake on Anticancer Therapy in Rats With Valine-depleted Amino Acid Imbalance", Nutrition and Cancer, vol. 28, No. 1, pp. 107-112.

Komatsu et al., "Effects of Valine-Depleted Total Parenteral Nutrition on Fatty Liver Development in Bearing Rats", Nutrition, vol. 14, No. 3, 1998, pp. 276-281.

Walter H. Horl et al., "Effects of High doses of leucine and ketoleucine on glycogen and protein metabolism in acute uremia", The American Journal of Clinical Nutrition, vol. 33, Jul. 1980, pp. 1468-1475.

\* cited by examiner

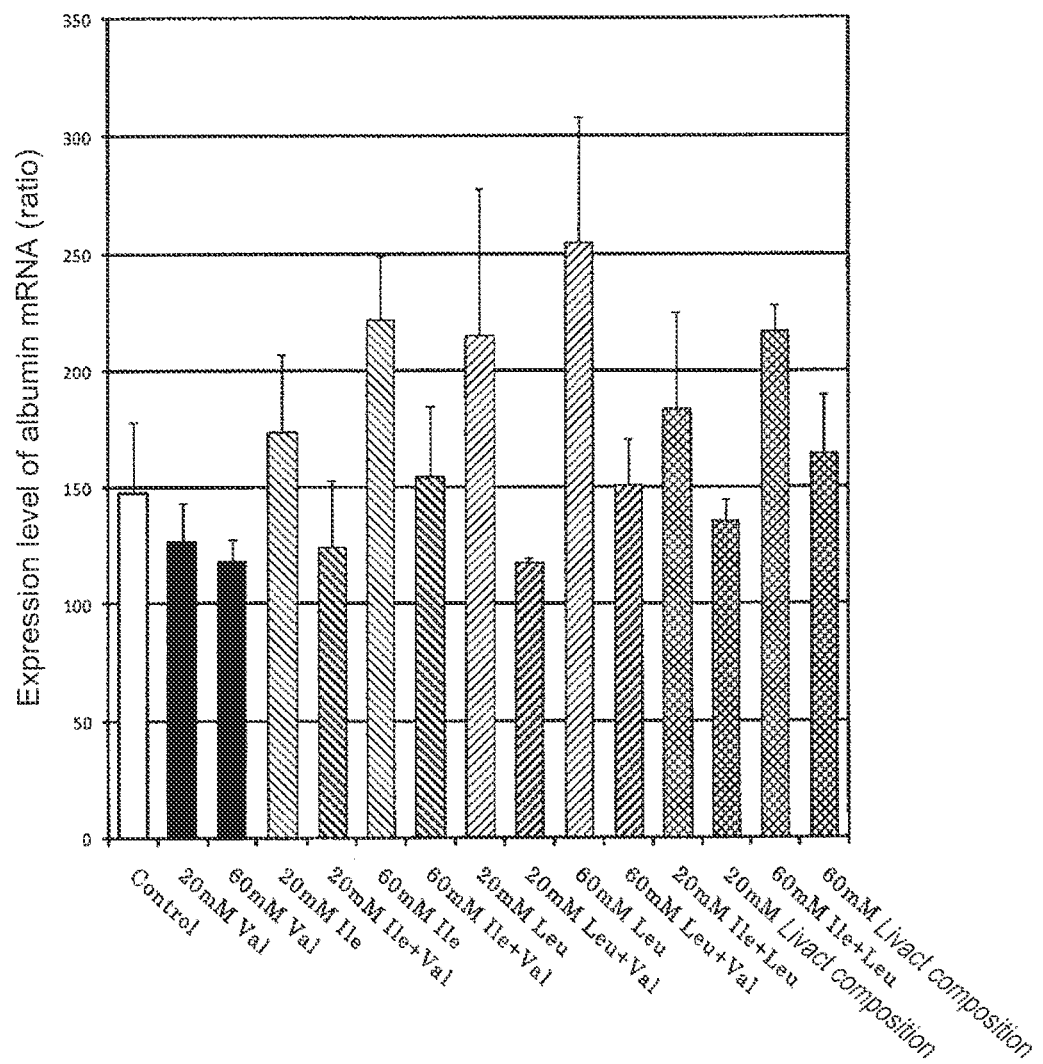

COMPOSITION FOR AMELIORATION OF HYPOALBUMINEMIA

The present application is a divisional of U.S. application Ser. No. 13/638,358, which is a National Stage of International Patent Application No. PCT/JP2011/058365 filed Mar. 31, 2011, which claims priority to Japanese Application No. 2010-089077 filed Apr. 7, 2010. The disclosures of U.S. application Ser. No. 13/638,358 and International Patent Application No. PCT/JP2011/058365 are incorporated by reference herein in their entireties.

SEQUENCE LISTING

The instant application contains a Sequence Listing, which has been submitted electronically in ASCII format and is hereby incorporated by reference in its entirety. Said ASCII copy, created on Sep. 28, 2012, is named P42537.txt and is 1855 bytes in size.

TECHNICAL FIELD

The present invention relates to a composition for ameliorating hypoalbuminemia, and particularly relates to a composition for ameliorating hypoalbuminemia for preferred use in forms such as an infusion formulation, an oral formulation and a food or drink.

BACKGROUND ART

Conventionally, amino-acid preparations containing a branched-chain amino acids have been widely used for the purpose of ameliorating hypoalbuminemia and the like caused by a hepatic disease, etc. Such amino-acid preparations for ameliorating hypoalbuminemia containing a branched-chain amino acids are required to have an albumin production promotive effect as an efficacy index and reductions of side effects as a safety index. Three amino acids, valine, leucine and isoleucine are branched-chain amino acids. For example, Livact (registered trade mark) is an example of amino-acid preparations containing all of these valine, leucine and isoleucine as active ingredients, and is widely used.

Such conventional amino-acid preparations containing all of the three branched-chain amino acids have not yet satisfied requirement of clinical practice for the hypoalbuminemia amelioration effect on a hepatic disease patient. In of the aforementioned efficacy, development of a new medicinal drug and food further ameliorating hypoalbuminemia has been needed.

Furthermore, conventional amino-acid preparations containing all of the three branched-chain amino acids may develop side effects such as nausea, a feeling of fullness in the abdomen, diarrhea, constipation, abdominal discomfort, abdominal pain, vomiting, inappetence and heartburn. These side effects are due to a heavy protein load in the body. Therefore, a conventional amino-acid preparations containing a large amount of protein may reduce compliance. Specifically, also from the aforementioned safety point of view, it has been desired to develop a drug and food for ameliorating hypoalbuminemia having few side effects and good compliance.

Then, from the aforementioned efficacy and safety points of view, a technique has been proposed in consideration of interactions such as an additive action, a synergistic action and an antagonistic action between active ingredients such as valine, leucine and isoleucine in the above amino-acid preparation. For example, Japanese Patent No. 3712539 discloses a composition containing L-valine alone as an active ingredient, for improving or treating hypoalbuminemia associated with deterioration in liver function. Such a composition is characterized by containing no amino acids except L-valine as an active ingredient, and said to have few side effects and be able to e.g., improve a hepatic disease, etc.

However, the above conventional amino-acid preparation and the composition disclosed in Japanese Patent No. 3712539 cannot sufficiently exert an efficacy that an amino-acid preparation is expected to have, particularly, an albumin production promotive effect. In other words, a highly safe amino-acid preparation, etc. having fewer side effects while exerting a high albumin production promotive effect has not yet been provided.

PRIOR ART DOCUMENT

Patent Document

Patent Document 1: Japanese Patent No. 3712539

SUMMARY OF THE INVENTION

Object to be Solved by the Invention

The present invention was made in view of these disadvantages and is directed to providing a highly safe composition for ameliorating hypoalbuminemia exerting a high albumin production promotive effect as well as having fewer side effects.

Means to Solve the Object

The present inventors presumed that valine among the branched-chain amino acids, i.e., valine, leucine and isoleucine, may have an antagonistic action (inhibitory action) against the albumin production promotive effect of leucine and isoleucine in human hepatocytes, and consequently found that a composition containing leucine and/or isoleucine except valine as an active ingredient has a particularly high albumin production promotive effect in the level of human hepatocytes.

As a result, the invention made to solve the above problems is directed to a composition for ameliorating hypoalbuminemia containing a branched-chain amino acid as an active ingredient, wherein the composition contains leucine and/or isoleucine and does not contain valine as the active ingredient.

Since the composition for ameliorating hypoalbuminemia does not substantially contain valine, the antagonistic action of valine against the albumin production promotive effect of other active ingredients, i.e. leucine and/or isoleucine, is eliminated. As a result, other active ingredients except valine can effectively exert a high albumin production promotive effect. Furthermore, since the composition for ameliorating hypoalbuminemia does not substantially contain valine as an active ingredient, the protein load can be reduced just by the amount of valine, with the result that side effects can be reduced and safety can be improved. Particularly, the composition for ameliorating hypoalbuminemia, which does not contain valine in an amount corresponding to the amount of active ingredient, can greatly reduce a substantial glucose load on a hepatic disease patient, who is in the state of impaired glucose tolerance, and is also useful in blood glucose control.

The composition for ameliorating hypoalbuminemia preferably contains leucine and isoleucine as the branched-chain amino acid. As described, since the composition for ameliorating hypoalbuminemia contains both of leucine and isoleucine as the branched-chain amino acid, the albumin production promotive effects that leucine and isoleucine separately have can be exerted in an additive manner.

As described, in the case where leucine and isoleucine are contained as the branched-chain amino acid, the mass ratio of leucine to isoleucine is preferably from 0.1 to 10. By thus setting the mass ratio of leucine to isoleucine within the above range, the aforementioned albumin production promotive effect improved in an additive manner can be effectively exerted.

Furthermore, the composition for ameliorating hypoalbuminemia may contain either leucine or isoleucine alone as the branched-chain amino acid. By thus preparing the composition to contain either leucine or isoleucine alone, an in vivo protein load can be further more reduced and the balance between efficacy and safety can be maintained, for example, depending upon the state of a hepatic disease patient.

The composition for ameliorating hypoalbuminemia is preferably used in a form of infusion formulation. By thus preparing the composition for ameliorating hypoalbuminemia in a form of infusion formulation, the composition for ameliorating hypoalbuminemia can be rapidly and effectively administered intravascularly.

The composition for ameliorating hypoalbuminemia is preferably used in a form of oral formulation. By thus preparing the composition for ameliorating hypoalbuminemia in a form of oral formulation, the composition for ameliorating hypoalbuminemia can be easily and simply administered in a noninvasive mariner to a living body.

The composition for ameliorating hypoalbuminemia can be used in a form of food or drink. By thus preparing the composition for ameliorating hypoalbuminemia in a form of food or drink, the composition for ameliorating hypoalbuminemia can be further more easily and simply administered compared to the above oral formulation and particularly can contribute to improvement of QOL (Quality Of Life).

Herein, the term "branched-chain amino acid", which refers to the three essential amino acids, leucine, isoleucine and valine, is a concept including also these salts peptides or derivatives thereof. The "active ingredient" refers to a component contained in an amount sufficiently to exert an albumin production promotive effect, by itself.

Effect of the Invention

As explained in the above, the composition for ameliorating hypoalbuminemia of the present invention contains a branched-chain amino acid as an active ingredient. Since valine is not substantially contained as the branched-chain amino acid, if the composition is used in the form of e.g., a preparation, a high albumin production promotive effect is exerted; at the same time, high safety is shown due to fewer side effects. In particular, since a substantial glucose load on a hepatic disease patient, who is in the state of impaired glucose tolerance, can be significantly reduced, the aforementioned conventional problems can be sufficiently solved.

Specifically, the composition for ameliorating hypoalbuminemia can prevent or improve hypoalbuminemia caused by a reduction in exogenous intake of nutrition by indigestion and malnutrition, low nutrient conditions after surgical operations, a reduction in protein production in hepatic diseases such as hepatitis and cirrhosis; leakage of in vivo proteins out of the body observed in e.g., nephrosis syndrome and protein-losing gastroenteropathy and burn; hypercatabolism of in vivo proteins observed in diseases such as serious infection, fever, hyperthyroidism and malignant tumors; and a large amount of pleural effusion and ascites fluid storage, anasarca, and burn. Furthermore, the composition for ameliorating hypoalbuminemia can prevent or improve symptoms such as leg cramps, lung edema, ascites fluid and edema caused by the hypoalbumin state as mentioned above.

BRIEF DESCRIPTION OF DRAWING

FIG. 1 is a graph showing the results of Experiment 1.

MODE FOR CARRYING OUT THE INVENTION

Now, embodiments of the invention will be described in detail, below.

(Composition for Ameliorating Hypoalbuminemia)

The composition for ameliorating hypoalbuminemia contains a branched-chain amino acid as an active ingredient, wherein the composition contains leucine and/or isoleucine and does not contain valine as the active ingredient.

As described above, since the composition for ameliorating hypoalbuminemia does not substantially contain valine as an active ingredient, although details of the mechanism are unknown, it is considered that the composition has the following working effects (A) and (B).

(A) Valine is an inhibitory factor of other substances serving as active ingredients such as leucine, and presumed to have an antagonistic action against an albumin production promotive effect exerted by the active ingredients such as leucine in vivo. Accordingly, the composition for ameliorating hypoalbuminemia substantially contains no valine as an active ingredient, thereby completely eliminating an antagonistic action of valine against an albumin production promotive effect of leucine and/or isoleucine. As a result, it is considered that an active ingredient except valine, such as leucine can effectively exert a high albumin production promotive effect in vivo.

(B) Since the composition for ameliorating hypoalbuminemia substantially contains no valine, a protein load can be reduced just by the content of valine, particularly when it is used in a form of preparation. Because of this, the composition for ameliorating hypoalbuminemia can reduce side effects such as digestive-system symptoms and renal-system symptoms, which are produced when a conventional amino-acid preparation containing all of the three branched-chain amino acids is administered in vivo, and improve safety. Particularly valine in the three branched-chain amino acids is only one glucogenic amino acid enhancing a blood glucose level by taking it. When a hepatic disease patient takes a conventional amino-acid preparation containing such a glucogenic amino acid, valine, the hepatic disease patient may have a side effect of further increasing a post-meal blood glucose level. In contrast, since the composition for ameliorating hypoalbuminemia substantially contains no valine as an active ingredient, a substantial glucose load on a hepatic disease patient, who is in an impaired glucose tolerance condition, can be significantly reduced. This is also useful in blood glucose control.

Examples of isomers of the above branched-chain amino acid include, but not particularly limited to, L-form, D-form and DL-form. Of these, an L-form branched-chain amino acid isomer, which has affinity for synthesis of albumin protein in vivo, is preferably used.

The forms of the branched-chain amino acids as mentioned above are not particularly limited and include, for example, a free pure crystalline amino acid, a salt, a peptide or a derivative thereof. Examples of the salt form of the branched-chain amino acid include pharmacologically acceptable salt forms such as a sodium salt, a potassium salt, a hydrochloride and an acetate. Furthermore, examples of the peptide form of the branched-chain amino acids include a peptide of the branched-chain amino acids such as a dipeptide and a tripeptide thereof. As described, if the above branched-chain amino acids are converted to peptides, these peptides are hydrolyzed by the action of in vivo peptidase into free amino acids, which can be effectively used. Furthermore, examples of the derivatives of branched-chain amino acids include N-acetyl-DL-leucine, DL-norleucine, N-acetyl-DL-isoleucine, 4-hydroxy-L-isoleucine and β-methylnorleucine. These derivatives are decomposed by the action of in vivo acylase, etc. into free amino acids, which can be effectively used.

The composition for ameliorating hypoalbuminemia preferably contains both leucine and isoleucine as the branched-chain amino acid. As described, since both leucine and isoleucine are contained as the branched-chain amino acid, particularly when the composition for ameliorating hypoalbuminemia is used in a form of preparation, the albumin production actions of leucine and isoleucine do not mutually antagonized and an albumin production promotive effect in vivo can be improved in an additive manner.

The composition for ameliorating hypoalbuminemia may contain either leucine or isoleucine alone as the branched-chain amino acid. By thus preparing the composition for ameliorating hypoalbuminemia to contain either leucine or isoleucine alone, the composition, particularly when it is used in a form of preparation, can further reduce the protein load in vivo and effectively reduce side effects.

Accordingly, the composition for ameliorating hypoalbuminemia, if efficacy is emphasized when it is administered to, for example, a hepatic disease patient, may preferably contain both leucine and isoleucine with an intention to improve the aforementioned albumin production promotive effect in an additive manner. In contrast, if safety is emphasized when administered to, for example, a hepatic disease patient, the composition for ameliorating hypoalbuminemia may contain only either leucine or isoleucine alone with an intention to effectively reduce side effects by decreasing the aforementioned protein load. In short, the composition for ameliorating hypoalbuminemia can maintain the balance between efficacy and safety depending upon the state of a hepatic disease patient.

The mass ratio of leucine to isoleucine is preferably from 0.1 to 10, and more preferably, from 0.5 to 3.0. By thus setting the mass ratio of leucine to isoleucine within the above range, the composition for ameliorating hypoalbuminemia can exert an effect of improving the aforementioned albumin production promotive effect in an additive manner without fail.

(Optional Components)

The composition for ameliorating hypoalbuminemia may contain additives other than the aforementioned branched-chain amino acid, if necessary, as long as they do not damage the Effect of the Invention. Examples of the additives include pharmaceutically or food hygienically acceptable amino acids, a stabilization agent, a preservative, a solubilization agent, a pH regulator, a thickener, an antioxidant, a coloring agent, a flavor and an artificial sweetener. The contents of these additives may be appropriately set in accordance with the content of the aforementioned branched-chain amino acid.

(Form of Preparation)

The composition for ameliorating hypoalbuminemia is preferably used in a form of preparation. Examples of the form of such a preparation include, but not particularly limited to, an infusion formulation, an oral formulation, a transdermal absorption preparation, a suppository, an adhesive skin patch, an ointment, a poultice and a lotion.

Particularly, the composition for ameliorating hypoalbuminemia is preferably prepared in a form of infusion formulation. BY thus preparing the composition for ameliorating hypoalbuminemia in a form of infusion formulation, the composition for ameliorating hypoalbuminemia can be rapidly and effectively administered intravascularly and the albumin production promotive effect in vivo can be exerted most highly.

Examples of types of the infusion formulation include, for example, an injection and an intravenous fluid. When the composition for ameliorating hypoalbuminemia is prepared in a form of injection or an intravenous fluid, these are preferably sterilized and controlled to be isotonic to blood. Furthermore, in preparing the composition for ameliorating hypoalbuminemia in a form of injection or an intravenous fluid, as a diluent, for example, water, ethyl alcohol, polyethylene glycol, propylene glycol, ethoxylated isostearyl alcohol, polyoxyisostearyl alcohol and polyoxyethylene sorbitan fatty acid ester can be used. Furthermore, a sufficient amount salt, glucose or glycerin to control the solution to be isotonic to the body fluid may be contained. Note that, the above infusion formulation can be cryopreserved or it can also be stored after removing a moisture content by lyophilization or the like. When such an infusion formulation lyophilized and stored is used, distillation water, sterilized water, or the like for injection is added to dissolve it again and then put in use.

The composition for ameliorating hypoalbuminemia can be also prepared in a form of oral formulation. By thus preparing the composition for ameliorating hypoalbuminemia in a form of oral formulation, the composition for ameliorating hypoalbuminemia can be easily and simply administered without invading a living body and an albumin production promotive effect can be sufficiently exerted in vivo.

Examples of types of the oral formulation include, but not particularly limited to, a tablet, a powder, a grain, a fine grain, a pill, a capsule, a troche, a chewable agent and a syrup. When the preparation is used in a form of tablet, various types of carriers known in the field of hypoalbuminemia amelioration are used. Examples of the carrier include excipients such as lactose, white sugar, sodium chloride, glucose, urea, starch, calcium carbonate, kaolin, crystal cellulose and silicate; binders such as water, ethanol, propanol, simple syrup, dextrose in water, starch liquid, gelatin solution, carboxymethylcellulose, shellac, methylcellulose, potassium phosphate and polyvinyl pyrrolidone; disintegrators such as dry starch, sodium alginate, powdered agar, powdered laminaran, sodium hydrogen carbonate, calcium carbonate, polyoxyethylene sorbitan fatty acid ester, sodium lauryl sulfate, monoglyceride stearate, starch and lactose; collapse suppressors such as white sugar, stearin, cacao butter and hydrogenated oil; absorption promoters such as quaternary ammonium base and sodium lauryl sulfate; humectants such as glycerin and starch; adsorbents such as starch, lactose, kaolin, bentonite and colloidal silicate; and lubricants such as purified talc, stearate, powdered boric acid and polyethylene glycol. Furthermore, these tablets can be prepared, if necessary, in the form of general coating tablets such as a sugar coating tablet, a gelatin coating tablet, an enteric coating tablet, a film coating tablet, a double coating tablet and a multi-coating tablet.

Furthermore, when the preparation is used in a form of pill, various types of carriers known in the field of hypoalbuminemia amelioration are used. Examples of the carriers include excipients such as glucose, lactose, starch, cacao butter, hydrogenated vegetable oil, kaolin and talc; binders such as powdered gum Arabic, powdered tragacanth, gelatin and ethanol; laminaran and agar.

The aforementioned oral formulation may further contain additives. Examples of such additives include a surfactant, an absorption promoter, a filler, an extending agent, a moisturizer, a preservative, a stabilizer, an emulsifier, a solubilization agent and a salt controlling osmotic pressure. These can be appropriately selected depending upon the dosage unit form of the oral formulation and put in use.

(Form of Food or Drink)

The composition for ameliorating hypoalbuminemia is preferably used in a form of food or drink. By thus using the composition for ameliorating hypoalbuminemia in a form of food or drink, the composition can be further more easily and simply administered than the aforementioned oral formulation and an albumin production promotive effect in vivo can be sufficiently exerted. Furthermore, by preparing the composition for ameliorating hypoalbuminemia in a form of food or drink, the composition can be particularly easily and simply taken in daily life, contributing to improvement of QOL (Quality Of Life).

Examples of the aforementioned food or drink include, but not particularly limited to, a supplement, food with nutrient function claims, food for specified health use and food for sick person. Furthermore, examples of form of the aforementioned food or drink include a powder, a grain and a beverage such as a drink, capsule, a tablet including a chewable agent and edible film. Note that, a method for producing these foods and drinks is not particularly limited as long as it may not damage the Effect of the Invention and a method those skilled in the art employ in each use can be employed.

Of the aforementioned foods and drinks, in the case of a granular food, the size of the grain is preferably about 20 µm or more and 2000 µm or less, more preferably, about 100 µm or more and 1500 µm or less and particularly preferably, about 500 µm or more and 1000 µm or less. Such a granular food can be taken in a granular state together with a beverage such as water, tea and juice and also taken by dissolving it in a beverage.

Note that, the composition for ameliorating hypoalbuminemia of the present invention is not limited to the aforementioned embodiment. For example, if the form of the composition for ameliorating hypoalbuminemia of the present invention is an oral formulation or a food or drink, if necessary, an adhesive (thickening agent, gelatinizer) may be added to prepare the composition in a gelatin form or jelly form. By thus preparing the composition for ameliorating hypoalbuminemia of the present invention in a gelatin form or jelly form, oral administration can be easily performed and gastrointestinal absorption becomes satisfactory. Examples of type of the adhesive include, but not particularly limited to, agar, gelatin, carrageenan, Arabian gum, guar gum, locust bean gum, Tara gum, gellan gum, curdlan, xanthan gum, pullulan, pectin, sodium alginate, carboxymethylcellulose, and others such as a polysaccharide that can be usually used as an adhesive. These may be used alone or in combination of two or more Note that, as the blending ratio of such an adhesive, a ratio of 5 or less parts by mass relative to the composition for ameliorating hypoalbuminemia (100 parts by mass) prepared into gelatin form or jelly form.

EXAMPLES

Now, the present invention wall be more specifically described based on Examples; however, the present invention is not restrictively interpreted based on the description of these Examples.

<Effect on Albumin mRNA Expression and Albumin Secretion Level of Cultured Human Hepatocytes>

In this test, human primary cultured hepatocytes were cultured by each test solution to check a change of albumin mRNA expressional potency and a change of secretion level of albumin. The test was performed as follows.

<Measurement Item>

(1) Albumin mRNA and Hypoxanthine Phosphoribosyltransferase 1 (Hereinafter Referred to Simply as "HPRT1") mRNA Albumin mRNA and HPRT1 mRNA were measured. The nucleotide sequences of albumin and HPRT1 are registered in the GenBank as follows and each nucleotide sequence follows the sequence registered.

Albumin; GenBank accession number XM 031322

HPRT1; GenBank accession number NM 000194

Note that, HPRT1, which is a house keeping gene serving as a control, was measured in the same test. The sequences of primers and probes used in measurement of albumin are made public in Nishimura, M., Yoshitsugu, H., Yokoi, T., Tateno, C., Kataoka, M., Horie, T., Yoshizato, K. and Naito, S.: Evaluation of mRNA expression of human drug-metabolizing enzymes and transporters in chimeric mouse with humanized liver. Xenobiotica, 35: 877-890 (2005). Furthermore, the sequences of primers and probes used in measurement of HPRT1 are made public in Nishimura, M., Naito, S. and Yokoi, T.: Tissue-specific mRNA expression profiles of human nuclear receptor subfamilies. Drug Metab. Pharmacokinet., 19: 135-149 (2004).

(2) Albumin Concentration in Medium

Albumin concentration in a medium was measured by a Human Albumin EIA Kit (manufactured by Takara Bio Inc.).

<Substances Subjected to Test>

The following substances were used.

Isoleucine (Ile): MW 131.17

Leucine (Leu): MW 131.17

Valine (Val): MW 117.15

<Hepatocytes Subjected to Test>

As hepatocytes, human normal hepatocytes (Human Normal Hepatocytes, Lot.100, LMP, ONQ and VUA, manufactured by In Vitro Technologies, Inc.) were used.

<Reagents>

The following reagents and instruments were used.

Normal hepatocyte specific medium kit: Cambrex Corporation (Takara Bio Inc.)

Hank's Balanced. Salt solution Modified: Sigma (company), 500 mL

HEPES Buffer (1 M): 100 mL

Sodium Pyruvate Solution (100 mM): 100 mL

Acrodisc Syringe Filters: Pall Corporation, product number 4187, 50 filters per set Rneasy Mini Kit (50): QIAGEN QIAshredder (50): QIAGEN
Yeast tRNA: GIBCO BRL
TaqMan One-Step RT-PCR Master Mix Reagents Kit: Applied Biosystems
Fast 96-Well Reaction Plate (0.1 mL): Applied Biosystems
Optical Adhesive Covers: Applied Biosystems
24 well flat-bottom plate (Collagen type I coat): AGC Techno Glass Co., Ltd.
15 mL Conical Tube: Falcon
Trypan blue: Flow Laboratories LTD., 0.4% solution in 0.85% saline
β-mercaptoethanol: Sigma (company)
Human Albumin EIA Kit: Takara Bio Inc.

Furthermore, mRNA was quantified by use of the primer pairs and probe represented by individual sequences (the position of initiation codon follows the each nucleotide sequence registered) shown in the following Table 1 and in accordance with RT-PCR (Real-time quantitative reverse transcription-polymerase reaction). Each of the primers and probe was prepared by an automatic DNA synthesizer.

TABLE 1

| Type | | Nucleotide Sequence | Position from initiation codon |
|---|---|---|---|
| Albumin | forward primer | SEQ ID NO: 1 | 1281-1302 |
| | reverse primer | SEQ ID NO: 2 | 1383-1363 |
| | probe | SEQ ID NO: 3 | 1305-1334 |
| HPRT1 | forward primer | SEQ ID NO: 4 | 139-159 |
| | reverse primer | SEQ ID NO: 5 | 238-218 |
| | probe | SEQ ID NO: 6 | 174-199 |

<Preparation of Solution>
(1) Preparation of 50 μg/mL Yeast tRNA Solution
Yeast tRNA was diluted with RNase free water up to a concentration of 50 μg/mL.
(2) Preparation of Various Types of Test Solutions Each Containing a Test Substance.
(2-1) Buffer A
As Buffer A, Hank's Balanced Salt solution Modified, HEPES Buffer (1 N) and Sodium Pyruvate Solution (100 mM) were blended in a ratio of 100:1:2.
(2-2) Buffer B
As Buffer B, Buffer A and a medium were blended in the ratio of 9:1.
(2-3) Test Solution of the Livact Composition
As the test solution of the Livact composition, a Livact composition was dissolved such that the concentrations of Ile, Leu, and Val became 13.8 mM, 27.7 mM, and 18.5 mM, respectively after blending (60 mM as the concentration of the Livact composition test solution). Note that, in the dissolution procedure, a Livact composition was dissolved in Buffer A and then a medium was added in an amount 1/10 as low as that of Buffer A.
(2-4) Ile, Leu or Val Solution
As an Ile, Leu or Val solution, Ile, Leu or Val was dissolved so as to have a concentration of 60 mM. Note that, in the dissolution procedure, Ile, Leu or Val was dissolved in Buffer A and then a medium was added in an amount 1/10 as low as that of Buffer A.
(2-5) Control
The Livact composition test solution prepared in Section (2-3) and Ile, Leu or Val solution prepared in Section (2-4) were diluted 3 fold with Buffer B to prepare a 20 mM solution.

<Primary Culture of Human Normal Hepatocyte>
According to a method of Nishimura et al. (Nishimura, M., Yoshitsugu, H., Naito, S. and Hiraoka, I.: Evaluation of gene induction of drug-metabolizing enzymes and transporters in primary culture of human hepatocytes using high-sensitivity real-time reverse transcription PCR. Yakugaku Zasshi, 122: 339-361 (2002)), $1 \times 10^5$ cells/400 μL was dispensed in each well of a 24 well plate and cultured in a $CO_2$ incubator. After 3 hours, medium exchange was performed. Further after 21 hours (24 hours after inoculation), medium exchange was performed. Thereafter, the medium was exchanged every 24 hours. Note that, the amount of liquid medium to be exchanged was set at 400 μL/well. Furthermore, exchange to each test solution was performed at the after 48 hours at which medium exchange was performed.

<Experiment 1>
After human hepatocytes ($1 \times 10^5$ viable cells/0.4 mL/well) were inoculated, medium exchange was performed 3 hours and 24 hours after inoculation. Note that, the viability at the inoculating time was 90.4% (Lot 100). Then, 48 hours after inoculation, a test substance was added and 24 hours after addition of the test substance was initiated, Total RNA was extracted (using Rneasy Mini Kit). Quantification of mRNA of albumin and HPRT1 was performed by real time RT-PCR. Note that, HPRT1, which is a house keeping gene, was used as an internal standard.

<Experiment 2>
After human hepatocytes ($1 \times 10^5$ viable cells/0.4 mL/well) were inoculated, medium exchange was performed 3 hours and 24 hours after inoculation. Note that, the viability at the inoculating time were 93.6% (Lot 100), 84.2% (Lot LMP), 90.0% (Lot QNQ) and 84.3% (Lot VUA). Then, 48 hours after inoculation, a test substance was added and 24 hours after addition of the test substance was initiated, the medium was taken and the secretion level of albumin was measured.

<Preparation of Total RNA>
After the medium was suctioned, Total RNA was extracted by use of QIA shredder and Rneasy Mini Kit. Now, a preparation method using the Kit will be described below. At the time points of 3, 24, 48 and 72 hours after initiation of culturing, medium was removed by suction from each well of the 24 well plate. However, at the time point of zero, i.e., initiation of culturing, hepatocytes were taken in a 15 mL-Conical Tube so as to contain $2 \times 10^5$ cells/tube. After centrifuged, the medium was removed by suction. Next, a β-mercaptoethanol-containing RLT solution (RLT solution: β-mercaptoethanol=1:100) was added in an amount of 400 μL for each and pipetted. Thereafter the total amount was transferred in a QIA shredder column and centrifuged at 15,000 rpm for 2 minutes. The eluate (350 μL) was taken and the equivalent amount of 70% ethanol solution was added. After stirring for 10 seconds was repeated three times, the total amount was added to an Rneasy Mini spin column and centrifuged at 12,000 rpm for 30 seconds and the eluate within a Collection tube was removed by suction. A RW1 solution (700 μL) was added and centrifuged at 12,000 rpm for 30 seconds, and thereafter, the Collection tube was replaced. A RPE solution (500 μL) was added and centrifuged at 12,000 rpm for 30 seconds and thereafter the eluate within the Collection tube was removed by suction. A RPE solution (500 μL) was added and centrifuged at 15,000 rpm for 2 minutes. Thereafter, the collection tube was exchanged with a Collection tube (1.5 mL). Rnase free water (50 μL) was added and centrifuged at 10,000 rpm for 1 minute to elute total RNA. The eluate was diluted with a 50 μg/mL Yeast tRNA solution 5 fold to prepare a Total RNA solution for measurement. Note that, extraction operations were all performed room temperature. Furthermore, the 50 µg/mL Yeast tRNA solution was prepared by diluting a Yeast tRNA with RNase-free distillation water.

<Measurement of mRNA>

Applied Biosystems 7500 Fast Sequence Detection System (Applied Biosystems) was used to quantify mRNA of the house keeping gene (HPRT1) and albumin, as follows.

RT-PCR was performed using TaqMan One-Step RT-PCR Master Mix Reagents Kit containing a 300 nM Forward Primer, a 900 nM Reverse Primer and 200 nM TaqMan Probe, in a system of 20 µL/tube. Total RNA solution (3 µL) was used. As RT-PCR conditions, the reaction mixture was maintained at 48° C. 30 minutes and thereafter at 95° C. for 10 minutes and then a cycle consisting of a reaction at 95° C. for 15 seconds and a reaction at 60° C. for 1 minute was repeated 40 times. Fluorescent intensity was measured every cycle. Note that, as a reaction container, a Fast 96-Well Reaction Plate (0.1 mL) was used and as a cover, Optical Adhesive Covers was used.

<Quantification of Albumin Secretion Level>

The albumin concentration in the medium was measured by a Human Albumin EIA Kit (Takara Bio Inc.).

<Calculation Method and Statistical Process of Results>

(I) Quantification of mRNA

HPRT1 mRNA was used as an endogenous control. Quantitative values of mRNA were calculated by the ΔCt method (Nishimura, M., Yaguri, H., Yoshitsugu, H., Naito, S. & Satoh, T., (2003); Yakuuaku Zasshi, 123, 369-375) and a test was performed in triplicate. The expression level of albumin mRNA was expressed by a ratio based on the expression level of HPRT1 mRNA (regarded as 1). The average value (mean)±a standard deviation (SD) was shown in Table 2 and FIG. 1.

<Quantification of Albumin Secretion Level>

The results were shown as values for each Lot and as an average value (mean)±a standard deviation (SD).

<Results and Discussion>

The obtained results are shown in Table 2, Table 3 and FIG. 1.

TABLE 2

| Test substance | Expression level of albumin mRNA (mean ± SD) |
|---|---|
| 1/10 medium (Control) | 148 ± 30 |
| 20 mM Ile | 174 ± 33 |
| 60 mM Ile | 222 ± 27 |
| 20 mM Leu | 215 ± 63 |
| 60 mM Leu | 255 ± 53 |
| 20 mM Val | 127 ± 17 |
| 60 mM Val | 118 ± 10 |
| 20 mM Ile + Leu (10 mM + 10 mM) | 184 ± 41 |
| 60 mM Ile + Leu (30 mM + 30 mM) | 217 ± 11 |
| 20 mM Ile + Val (10 mM + 10 mM) | 125 ± 28 |
| 60 mM Ile + Val (30 mM + 30 mM) | 155 ± 30 |
| 20 mM Leu + Val (10 mM + 10 mM) | 118 ± 2 |
| 60 mM Leu + Val (30 mM + 30 mM) | 151 ± 20 |
| 20 mM Livact composition | 136 ± 9 |
| 60 mM Livact composition | 165 ± 25 |

TABLE 3

1. Value of albumin secretion level in each Lot in Experiment 2

| | ng/well |
|---|---|
| Lot 100 60 mM Livact composition | 12.30 |
| Lot 100 Ile + Leu (30 mM + 30 mM) | 20.88 |
| Lot LMP 60 mM Livact composition | 2.06 |
| Lot LMP Ile + Leu (30 mM + 30 mM) | 3.22 |
| Lot ONQ 60 mM Livact composition | 4.92 |
| Lot ONQ Ile + Leu (30 mM + 30 mM) | 9.56 |
| Lot VUA 60 mM Livact composition | 7.44 |
| Lot VUA Ile + Leu (30 mM + 30 mM) | 9.96 |

2. Average value of albumin secretion levels in all Lots in Experiment 2

| | ng/well (mean ± SD) |
|---|---|
| 60 mM Livact composition | 6.68 ± 4.34 |
| Ile + Leu (30 mM + 30 mM) | 10.91 ± 7.33 |

From each table and graphs of FIG. 1 showing the results of Table 2, the following facts are found. That as shown in Table 2 and FIG. 1, using human hepatocytes, the effects of single use of Ile, Leu and Val, whether a combination of Ile and Leu, a combination of Ile and Val, and a combination of Leu and Val mutually produce an additive effect, a synergistic effect or mutually antagonize were investigated based an increase of albumin mRNA expression level as an index. A single amino acid of Ile, Leu and Val, combinations of Ile and Leu, Leu and Val, Ile and Val, and the Livact composition (Ile:Leu:Val=1:2:1.35, 20 mM, 60 mM) were compared. As a result, it was confirmed that in the cases of single amino acids of Ile and Leu and the combination of Ile and Leu, albumin mRNA expression level increases in an additive manner. It was found That the combination of Ile and Leu has an additive effect of albumin mRNA expression level. Furthermore, it was confirmed that in the cases of a combination with Val an increase effect of the albumin mRNA expression level is reversed.

Furthermore, Experiment 2 shows the results of 4 lots of human hepatocytes. If Val was contained, the secretion level decreased in the same manner as in Experiment 1 (see Table 3).

As described above, it is found that it is effective to use the composition for ameliorating hypoalbuminemia to increase an albumin synthetic ability.

<Study of the Effects on Increase of the Plasma Albumin Concentration in Hypoalbuminemia Mice>

In this test, the effects of each test substance on plasma albumin concentration of mice which had onset of hypoalbuminemia was measured. The test was performed as follows.

<Experiment 3>

BALB/c, female mice were induced hypoalbuminemia by fasting for 3 days. Each test substance was orally administered for 7 days and the plasma albumin concentration was measured. The details of the experiment will be shown below.

<Preparation of Test Substance>

Val (+):

L-leucine (0.214 g), L-isoleucine (0.107 g) and L-valine (0.129 g) (all obtained from the peptide laboratory) were weighed and placed together with an appropriate amount of distilled water for injection (Otsuka Pharmaceutical Co., Ltd.) in a 15 mL-conical tube (Japan, Becton, Dickinson and Company) and mixed. They were completely dissolved in the water to make 15 mL.

Val (−):

L-leucine (0.214 g) and L-isoleucine (0.107 g) (all obtained from the peptide laboratory) were weighed and placed together with an appropriate amount of distilled water for injection (Otsuka Pharmaceutical Co., Ltd.) in a 15 mL-conical tube (Japan, Becton, Dickinson and Company) and mixed. They were completely dissolved in the water to make 15 ml.

<Animal Used>

In this Experiment, mice, BALB/cCr Slc, female, 7 weeks old (body weight upon arrival: 18 g to 20 g) (Japan SLC, Inc.) were used.

<Administration Method>

The above mice were divided into the following three groups. The following valine (+) group and Val (−) group were fasted for 3 days, and each test substance prepared in the above was orally administered at a dose of 10 mL/kg/day, continuously for 7 days. Note that, the Val (+) group and the Val (−) group were fed during the period of administering each test substance. Furthermore, the control group was only fed during the whole test period.

(Val (+) Group)

The group of mice fasted for 3 days and then Val (+) was orally administered, n=3
    isoleucine: 0.071 g/kg/day,
    leucine: 0.143 g/kg/day,
    valine: 0.086 g/kg/day (Val (−) Group)

The group of mice fasted for 3 days and then Val (−) was orally administered, n=5
    isoleucine: 0.071 g/kg/day,
    leucine: 0.143 g/kg/day (Control Group)

The group of mice fed during the whole test period, n=5

<Sampling>

At the 3rd day after initiation of fasting and 1st, 3rd and 7th days after initiation of administrating a test substance, the above mice were scratched the eyeground with a heparin-treated Terumo Hematocrit capillary tube (Terumo Corporation) without anesthesia to take blood (about 20 μL). The collected blood was cooled on ice and centrifuged at 12000 rpm for 10 minutes to separate the plasma, and was subjected to the plasma albumin measurement.

<Method for Measuring Plasma Albumin>

The plasma albumin concentration was measured by using dry-chem slide ALB-P (FUJIFILM Medical, Inc.) in an automatic analyzer DRI-CHEM 7000 (FUJIFILM Medical, Inc.). The plasma albumin concentrations of mice to the 7th day after administrating the test substance were shown in Table 4

<Analysis Method>

With respect to values of each measurement item, an average value (mean)±standard deviation (S.D.) of each group was obtained. Furthermore, statistical analysis between the Val (+) group and the Val (−) group was performed by the Student t-test and analysis of variance of time-dependent changes. Note that, the significance level of the test was 5% (both sides). Data counting was performed by Microsoft Excel 2003 (Microsoft Co., Ltd.). As a statistical analysis software, EXSAS 7.6 (Arm Systex Co., Ltd.) was used.

TABLE 4

| | Plasma albumin concentration (g/dL) | | | |
|---|---|---|---|---|
| | 3rd day after | After administration of test substance | | |
| Test group | fasting | 1st day | 3rd day | 7th day |
| Val(−) group | 1.65 ± 0.26 | 2.62 ± 0.16 | 2.91 ± 0.15 | 2.98 ± 0.17 |
| Val(+) group | 1.76 ± 0.40 | 2.57 ± 0.26 | 2.77 ± 0.08 | 2.73 ± 0.06 |
| Control group | 2.94 ± 0.10 | 2.89 ± 0.31 | 2.81 ± 0.12 | 2.80 ± 0.27 |

<Results and Discussion>

As shown in Table 4, a test substance was given for 7 days to the fasted mice under the above conditions, was observed that Val (−) group shows an upward tendency of album (p=compared to Val (+) group at the 7th day. Furthermore, according to analysis of variance of time-dependent changes supplementarily performed, a significant difference was observed between groups and time periods. It was suggested that Val (−) can increase plasma albumin concentration with time compared to Val (+). From the results of this test, it was considered that removing Val from BCAA (Val (−)) can be expected the effect on increase blood albumin concentration exceeding that of a BCAA preparation (Val (+)) such as Livact (registered trade mark) presently used in clinical practice.

INDUSTRIAL APPLICABILITY

As mentioned above, the composition for ameliorating hypoalbuminemia of the present invention preferably used, for example, in a form of preparation such as an infusion formulation, an oral formulation and a food or drink.

The invention claimed is:

1. A method for ameliorating hypoalbuminemia comprising administering a composition that contains leucine and isoleucine in a mass ratio of from 1:1 to 2:1 and does not contain valine as an active ingredient to a patient having hypoalbuminemia.

2. The method for ameliorating hypoalbuminemia according to claim 1, comprising administering the composition intravascularly.

3. The method for ameliorating hypoalbuminemia according to claim 1, comprising administering the composition orally.

4. The method for ameliorating hypoalbuminemia according to claim 1, comprising administering the composition intravascularly.

5. The method for ameliorating hypoalbuminemia according to claim 1, comprising administering the composition orally.

6. The method for ameliorating hypoalbuminemia according to claim 1, wherein the mass ratio of the leucine to the isoleucine in the composition is 1:1.

7. The method for ameliorating hypoalbuminemia according to claim 1, wherein the mass ratio of the leucine to the isoleucine in the composition is 2:1.

* * * * *

UNITED STATES PATENT AND TRADEMARK OFFICE
CERTIFICATE OF CORRECTION

PATENT NO. : 9,693,982 B2  
APPLICATION NO. : 14/287954  
DATED : July 4, 2017  
INVENTOR(S) : Doi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 56 days.

Signed and Sealed this  
Twenty-fifth Day of September, 2018

Andrei Iancu  
*Director of the United States Patent and Trademark Office*

SEQUENCE LISTING

<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
     forward primer sequence for albumin

<400> SEQUENCE: 1
ccagaatgcg ctattagttc gt                                          22

<210> SEQ ID NO 2
<211> LENGTH: 21

-continued

```
<212> TYPE: DNA
<213> ORGANISM: Artificial Sequence
<220> FEATURE:
<223> OTHER INFORMATION: Description of Artificial Sequence: Synthetic
      reverse primer sequence for albumin

<400> SEQUENCE: 2
acatttgctg cccactttc c                                              21

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      probe sequence for albumin

<400> SEQUENCE: 3
caccaagaaa gtaccccaag tgtcaactcc                                    30

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      forward primer sequence for HPRT1

<400> SEQUENCE: 4
gaacgtcttg ctcgagatgt g                                             21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      reverse primer sequence for HPRT1

<400> SEQUENCE: 5
ccagcaggtc agcaaagaat t                                             21

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      probe sequence for HPRT1

<400> SEQUENCE: 6
aggccatcac attgtagccc tctgtg                                        26
```